United States Patent
Turgeman et al.

(10) Patent No.: US 10,575,746 B2
(45) Date of Patent: Mar. 3, 2020

(54) EPICARDIAL MAPPING

(71) Applicant: Biosense Webster (Israel) Ltd., Yokneam (IL)

(72) Inventors: Aharon Turgeman, Zichron Ya'acov (IL); Benjamin Cohen, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 145 days.

(21) Appl. No.: 15/842,070

(22) Filed: Dec. 14, 2017

(65) Prior Publication Data

US 2019/0183367 A1     Jun. 20, 2019

(51) Int. Cl.

| | |
|---|---|
| *A61B 5/044* | (2006.01) |
| *G06T 15/04* | (2011.01) |
| *A61B 5/04* | (2006.01) |
| *A61B 5/042* | (2006.01) |
| *A61B 5/06* | (2006.01) |
| *A61B 8/12* | (2006.01) |
| *A61B 18/14* | (2006.01) |
| *A61B 18/00* | (2006.01) |

(52) U.S. Cl.
CPC .......... *A61B 5/044* (2013.01); *A61B 5/04011* (2013.01); *A61B 5/04012* (2013.01); *A61B 5/0422* (2013.01); *A61B 5/063* (2013.01); *A61B 8/12* (2013.01); *A61B 18/1492* (2013.01); *G06T 15/04* (2013.01); *A61B 2018/00577* (2013.01); *A61B 2018/00839* (2013.01); *A61B 2562/0209* (2013.01); *G06T 2210/41* (2013.01)

(58) Field of Classification Search
CPC ....... A61B 5/044; A61B 8/12; A61B 5/04012; A61B 5/04011; G06T 15/04
USPC ......................................................... 600/508
See application file for complete search history.

(56) References Cited

U.S. PATENT DOCUMENTS

| | | | |
|---|---|---|---|
| 5,391,199 | A | 2/1995 | Ben Haim |
| 5,471,982 | A | 12/1995 | Edwards |
| 5,687,737 | A | 11/1997 | Branham et al. |
| 5,889,524 | A | 3/1999 | Sheehan |

(Continued)

FOREIGN PATENT DOCUMENTS

| | | |
|---|---|---|
| EP | 3200159 A1 | 8/2017 |
| WO | WO 9406349 | 3/1994 |

(Continued)

OTHER PUBLICATIONS

Extended European Search Report for corresponding European patent application No. EP 18212183.0, dated Feb. 28, 2019.

(Continued)

*Primary Examiner* — Brian T Gedeon
*Assistant Examiner* — Philip C Edwards

(57) ABSTRACT

Electroanatomic mapping of the epicardium includes acquiring first and second electroanatomic data from first and second epicardial locations, acquiring a closed 3-dimensional image of the epicardium and modeling the image as a 3-dimensional triangular mesh. The first and second locations align with front-facing triangles and rear-facing triangles of the mesh. The second locations are projected from the rear-facing triangles onto the closest front-facing triangles. The first and second electroanatomic data are displayed on the front-facing triangles and the closest front-facing triangles, respectively.

10 Claims, 10 Drawing Sheets

(56) References Cited

U.S. PATENT DOCUMENTS

| | | |
|---|---|---|
| 6,226,542 B1 | 5/2001 | Reisfeld |
| 6,295,464 B1 | 9/2001 | Metaxas |
| 6,301,496 B1 | 10/2001 | Reisfeld |
| 6,892,091 B1 | 5/2005 | Ben Haim |
| 7,471,973 B2 | 12/2008 | Rudy |
| 8,144,950 B2 | 3/2012 | Peters |
| 8,358,819 B2 | 1/2013 | Wu |
| 8,838,203 B2 | 9/2014 | van Dam |
| 9,101,333 B2 | 8/2015 | Schwartz |
| 9,177,373 B2 | 11/2015 | Dikici |
| 2001/0056289 A1 | 12/2001 | Sippensgroenewegen |
| 2004/0015194 A1 | 1/2004 | Ransbury |
| 2006/0173251 A1 | 8/2006 | Govari |
| 2007/0038078 A1 | 2/2007 | Osadchy |
| 2011/0152684 A1 | 6/2011 | Altmann |
| 2014/0107510 A1 | 4/2014 | Bogun |
| 2015/0018698 A1 | 1/2015 | Safran |
| 2015/0164356 A1 | 6/2015 | Merschon |
| 2015/0313555 A1* | 11/2015 | Nabutovsky ........... A61B 5/044 600/374 |
| 2016/0120426 A1 | 5/2016 | Urman |
| 2016/0192902 A1 | 7/2016 | Werneth |
| 2016/0354049 A1 | 12/2016 | Bar-Tal |
| 2017/0105680 A1 | 4/2017 | Shushan |
| 2017/0128138 A1 | 5/2017 | Gliner |
| 2017/0202515 A1 | 7/2017 | Zrihem |
| 2017/0221254 A1 | 8/2017 | Zar |

FOREIGN PATENT DOCUMENTS

| | | |
|---|---|---|
| WO | WO 9605768 | 2/1996 |
| WO | WO 9724981 | 7/1997 |

OTHER PUBLICATIONS

Ramanthan et al. *Noninvasive Electrocardiographic Imaging for Cardiac Electrophysiology and Arrhythmia*, Nature Medicine 10, 422-428, Mar. 14, 2004.

Modre et al. *Atrial Noninvasive Activation Mapping of Paced Rhythm Data*, J. Cardiovascular Electrophysiol, 14:712-719, Jul. 2003.

* cited by examiner

EPICARDIAL MAPPING

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but other-wise reserves all copyright rights whatsoever.

BACKGROUND OF THE INVENTION

1. Field of the Invention

This invention relates to detecting, measuring or recording bioelectric signals of the body. More particularly, this invention relates to analysis of electrical signals of the heart for diagnostic purposes.

2. Description of the Related Art

The meanings of certain acronyms and abbreviations used herein are given in Table 1.

TABLE 1

Acronyms and Abbreviations

| LAT | Local Activation Time |
| PDM | Potential Duration Map |
| FAM | Fast Anatomical Mapping |

Epicardial mapping of the wall of the heart to obtain functional electroanatomic maps of the external surface of the wall is useful for diagnosing certain conditions, such as Brugada Syndrome. Typical maps of this sort include maps of local activation time (LAT), unipolar, bipolar and potential duration maps (PDM). The mapping can be performed by substantially the same methods as mapping of a chamber of the heart, but in this case the mapping catheter is external to the heart.

In order to perform the mapping a mapping catheter is touched at multiple points on the external wall of the heart. Generally, only a portion of the external wall is contacted, involving a minority of the surface area. The fast anatomical mapping (FAM) algorithm is used for mapping the epicardial shape and the acquired points used for coloring the Map. Fast anatomical mapping is described, for example, in U.S. Patent Application Publication No. 2011/0152684 by Altmann et al., whose disclosure is incorporated herein by reference. The FAM technique automatically computes a surface that defines the extent of the movements of the sensor (or electrodes). Ideally, the surface would have no thickness, but in practice the surface bounds a volume within which, but not outside of which, the sensor (or electrodes) was moved.

SUMMARY OF THE INVENTION

As noted above, The FAM algorithm does not generate an ideal plane that is curved in 3-dimensional space and that accurately represents the epicardial surface, Rather, the FAM algorithm generates a closed 3-dimensional shape (having a volume), in the approximate form of a squashed banana or convex-concave lens. Some of the acquired measurements map to rear-facing surfaces of the FAM-produced volume, while others map to front-facing surfaces. This produces distortion in the spatial representation of the measurements. Moreover, besides containing spatial errors, electroanatomic maps based on the FAM-produced volume are misleading. The rear-facing portions of the shape are obscured by front-facing portions. Thus, the observer cannot see the results produced by measurements taken at points that map to the rear-facing portions of the shape and sees only results relating to front-facing points. This issue is solved by the algorithm described below.

There is provided according to embodiments of the invention a method, which is carried out by inserting a catheter into a pericardial space of a heart, acquiring electrical signals at locations on an epicardial surface of the heart, including first locations and second locations, deriving first electroanatomic data regarding the first locations and second electroanatomic data regarding the second locations from the signals, acquiring a closed 3-dimensional image of the heart, modeling the image as a 3-dimensional mesh of triangles, which includes rear-facing triangles and front-facing triangles. The method is further carried out by placing the first locations and the second locations in registration with the mesh wherein the first locations align with a first portion of the front-facing triangles and the second locations align with a portion of the rear-facing triangles, projecting the second locations onto a second portion of the front-facing triangles, and displaying the first electroanatomic data on the first portion of the front-facing triangles and the second electroanatomic data on the second portion of the front-facing triangles.

According to yet another aspect of the method, displaying includes constructing an electroanatomic map of the first locations and the second locations.

According to still another aspect of the method, projecting the second locations includes identifying respective closest front-facing triangles to the portion of the rear-facing triangles, and associating the second locations with the closest front-facing triangles.

Another aspect of the method includes constructing first vectors from the center of mass of the mesh to each of the triangles, constructing second vectors from each of the triangles toward the exterior of the mesh, calculating respective dot products of the first vectors and the second vectors, and identifying the triangles as front-facing triangles and rear-facing triangles when the dot products are positive and negative, respectively.

An additional aspect of the method includes deleting the rear-facing triangles from the mesh after projecting the second locations.

According to one aspect of the method, acquiring a closed 3-dimensional image is performed using a fast anatomical mapping algorithm.

According to a further aspect of the method, acquiring a closed 3-dimensional image is performed prior to inserting a catheter.

There is further provided according to embodiments of the invention an apparatus including a probe that is adapted for insertion into a pericardial space of a heart. The probe had an elongated body, a location sensor, an ultrasound imaging transducer, at least one mapping electrode disposed on a distal portion of the body and a memory having programs stored therein. The apparatus includes a display, and a processor linked to the display and which accesses the memory to execute the programs. The processor is connectable to receive inputs provided by the at least one mapping electrode and the ultrasound imaging transducer, wherein the programs cause the processor to perform the steps of:

acquiring electrical signals from the at least one mapping electrode at locations on an epicardial surface of the heart, including first locations and second locations, wherein the first locations and the second locations are determined from readings of the location sensor, deriving first electroanatomic data regarding the first locations and second electroanatomic data regarding the second locations from the signals, acquiring a closed 3-dimensional image of the heart using the ultrasound imaging transducer, modeling the image as a 3-dimensional mesh of triangles, including rear-facing triangles and front-facing triangles, placing the first locations and the second locations in registration with the mesh wherein the first locations align with a first portion of the front-facing triangles and the second locations align with a portion of the rear-facing triangles, projecting the second locations onto a second portion of the front-facing triangles, and displaying the first electroanatomic data on the first portion of the front-facing triangles and the second electroanatomic data on the second portion of the front-facing triangles.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Overview.

Figure 1:
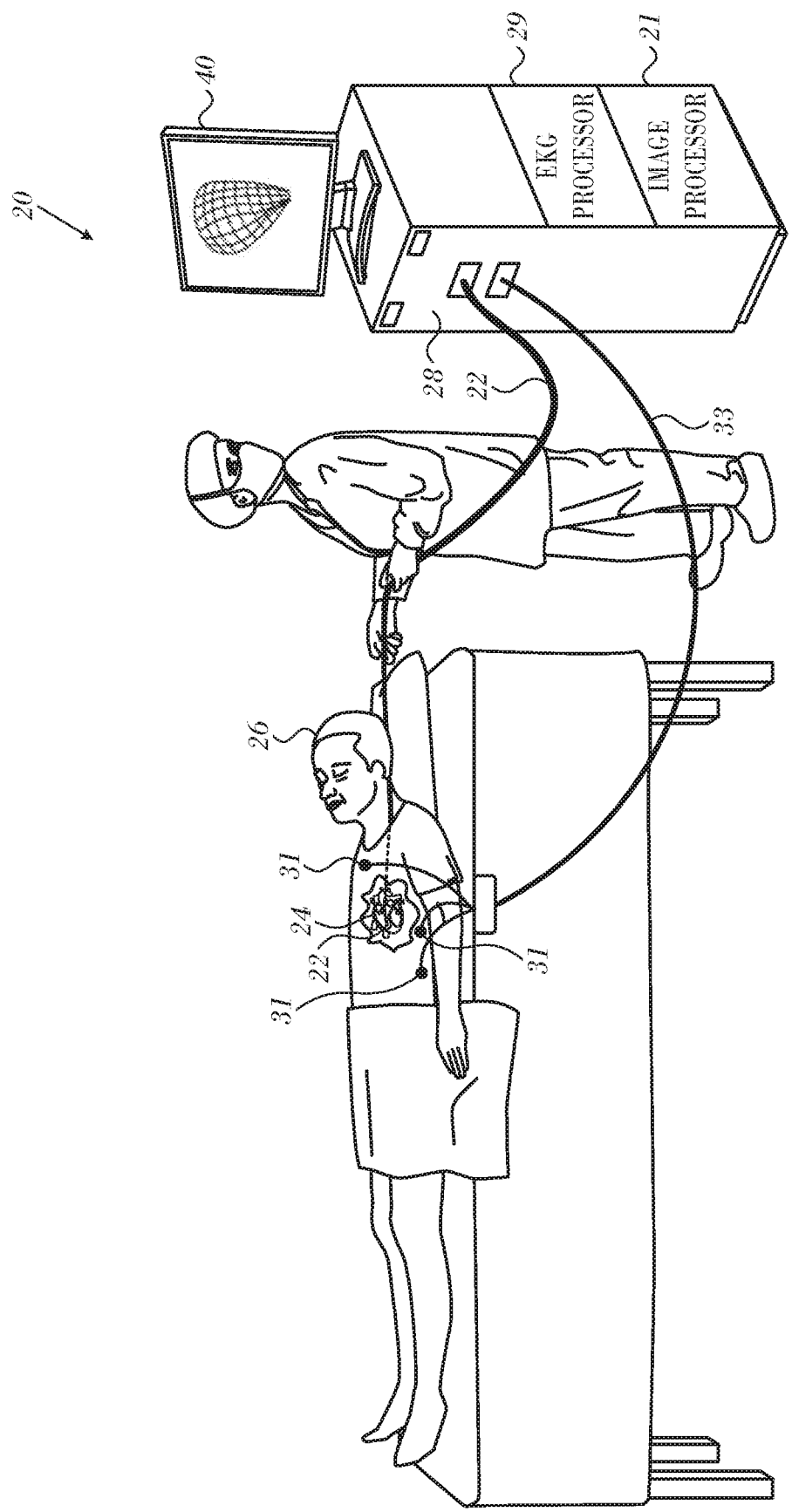
FIG. 1 is an illustration of a system, which is constructed and operative in accordance with a disclosed embodiment of the invention.

Turning now to the drawings, reference is initially made to FIG. 1, which is an illustration of a system 20, which is constructed and operative in accordance with a disclosed embodiment of the invention. The system 20 is used in determining the position of a probe or catheter 22, used for the acquisition of anatomic and electrical data, and for tissue ablation using the catheter 22. During acquisition of an endocardial electrical map, the catheter 22 is placed into chambers of a heart 24 of a subject 26 using a known intravascular approach. For obtaining an epicardial electrical map, the catheter 22 may be percutaneously inserted into the pericardial cavity that surrounds the heart 24. Alternatively, the epicardial electrical map may be obtained non-invasively. Exemplary methods and devices for cardiac mapping are described in U.S. Pat. Nos. 5,471,982, 5,391,199, 6,226,542, 6,301,496, and 6,892,091, and in PCT patent publications WO94/06349, WO96/05768 and WO97/24981, whose disclosures are incorporated herein by reference. U.S. Pat. No. 5,391,199, for example, describes a catheter including both electrodes for sensing cardiac electrical activity and miniature coils for determining the position of the catheter relative to an externally-applied magnetic field. Using this catheter data can be collected from a set of sampled points within a short period of time, by determining the electrical activity at a plurality of locations and determining the spatial coordinates of the locations.

The electrodes and transducers of distal end 44 of the catheter 22 are connected by a cable through the insertion tube of the catheter 22 to a control unit 28 (FIG. 1), which controls other elements of the system 20, including an image processor 21, and an EKG processor 29. The processors access a memory to execute programs stored therein for performing procedures detailed below. The control unit 28 determines position coordinates of the catheter 22 relative to specific landmarks or features of the heart 24. The control unit 28 drives a display 40, which shows the catheter position inside the body. The control unit 28 also drives the ablation transducers that are located generally at the tip of the catheter 22.

The catheter 22 is used in generating anatomic images or an epicardial electrical map. The distal end of the catheter 22 comprises an ultrasound imaging device, which is typically a phased array of transducers, well known in the art. The ultrasound imaging device is operated, as is known in the art, so as to capture a 2-dimensional "fan" image in the plane of the scanning ultrasonic beam (referred to as the "beam plane" or "image plane"), which contains the longitudinal axis of the catheter. The transducers receive ultrasonic waves that are reflected from objects in the beam plane and output signals in response to the reflected waves. Typically, these signals are conveyed by wires running through the catheter 22 to image processor 21, which processes the signals in order to form and display ultrasound images and 3-dimensional maps.

In some embodiments, the electrodes on the catheter can be used alternately for mapping and for ablation. One system that embodies the above-described features of the system 20 is the CARTO® 3 System, available from Biosense Webster, Inc., 33 Technology Drive, Irvine, Calif. 92618. This system may be modified by those skilled in the art to embody the principles of the invention described herein.

In some embodiments of the invention, epicardial electrical maps can be obtained noninvasively, using body-surface electrodes 31, of which three are shown representatively, it being known in the art that when using the noninvasive technique, much larger arrays of electrodes are typically required in order to obtain accurate epicardial electrical maps. The electrodes 31 may conveniently be mounted in multi-electrode chest panels as described in any of the following documents, all of which are herein incorporated by reference: Ransbury et al., U.S. Patent Application Publication No. 2004/0015194; Sippensgroenewegen, U.S. Patent Application Publication No. 2001/0056289; Ramanathan et al., in *Noninvasive Electrocardiographic Imaging for Cardiac Electrophysiology and Arrhythmia, Nature Medicine*, published online 14 Mar. 2004; and Modre et al. *Atrial Noninvasive Activation Mapping of Paced Rhythm Data*, J. Cardiovasc. Electrophysiology 14:712-719 (July 2003), The electrodes 31 are connected to the control unit 28 by a cable 33, and linked to the EKG processor 29.

Alternatively, the above-noted intrapericardial technique can be used to generate an epicardial electrical map. This method is still less invasive than intravascular catheterization technique for obtaining endocardial electrical maps. The technique employs an epicardial contact probe as the catheter 22, which is inserted through the chest wall into the pericardium, using known introduction techniques.

In either case, the epicardial electrical map typically shows the potentials on the epicardium, although it may also show endocardial potentials. Nevertheless, the term "epicardial electrical map" is employed herein, as the data of primary interest are obtained from outside the heart.

First Embodiment

Figure 2:
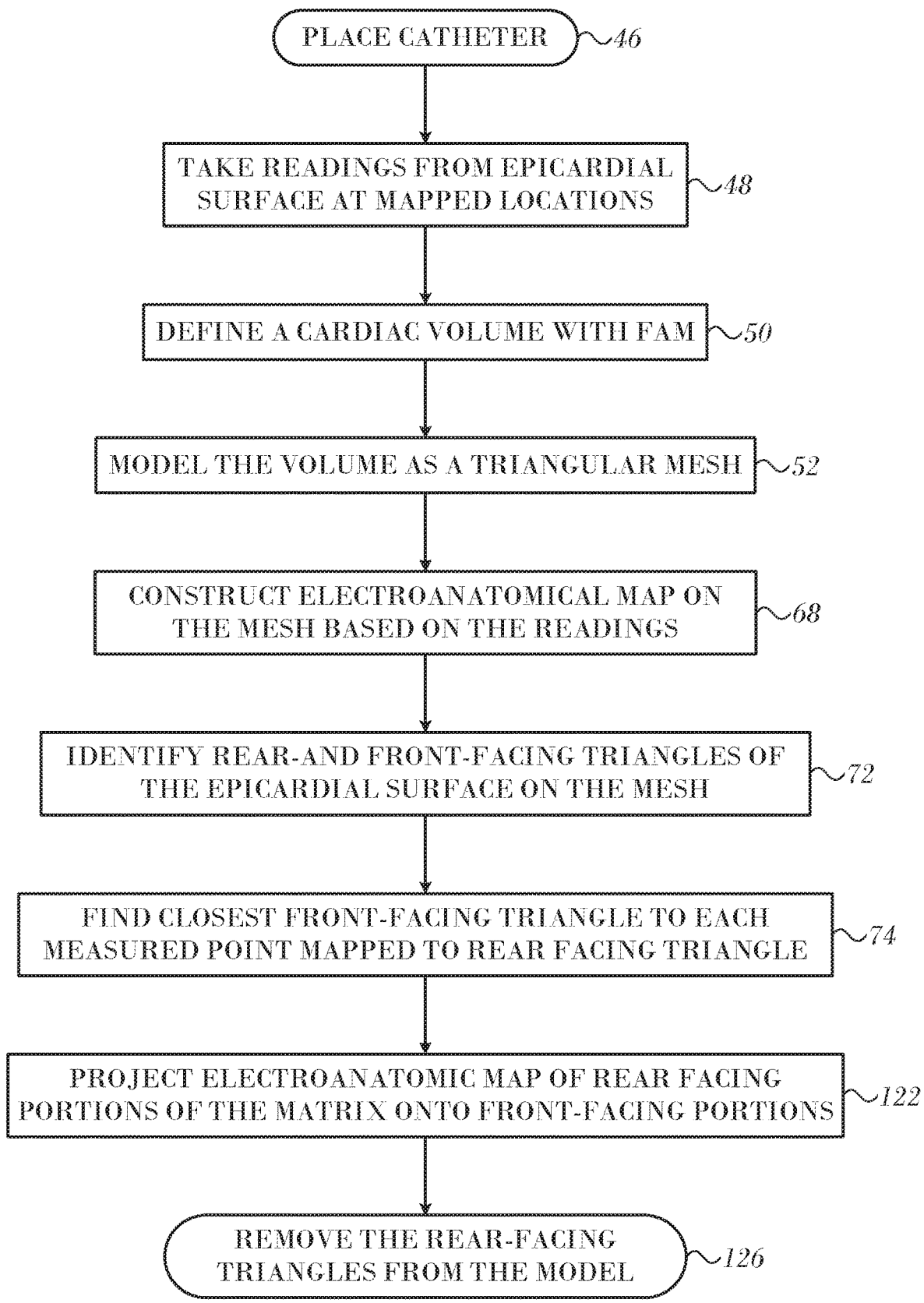
FIG. 2 is a flow chart of a method of electroanatomic mapping of the epicardium in accordance with an embodiment of the invention.

Reference is now made to FIG. 2, which is a flow chart of a method of electroanatomic mapping of the epicardium in accordance with an embodiment of the invention. The process steps are shown in a particular linear sequence in FIG. 2 for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At initial step 46 a mapping catheter is positioned at the epicardium. At step 48 electrical readings are at mapped locations are taken as described above.

Figure 3:
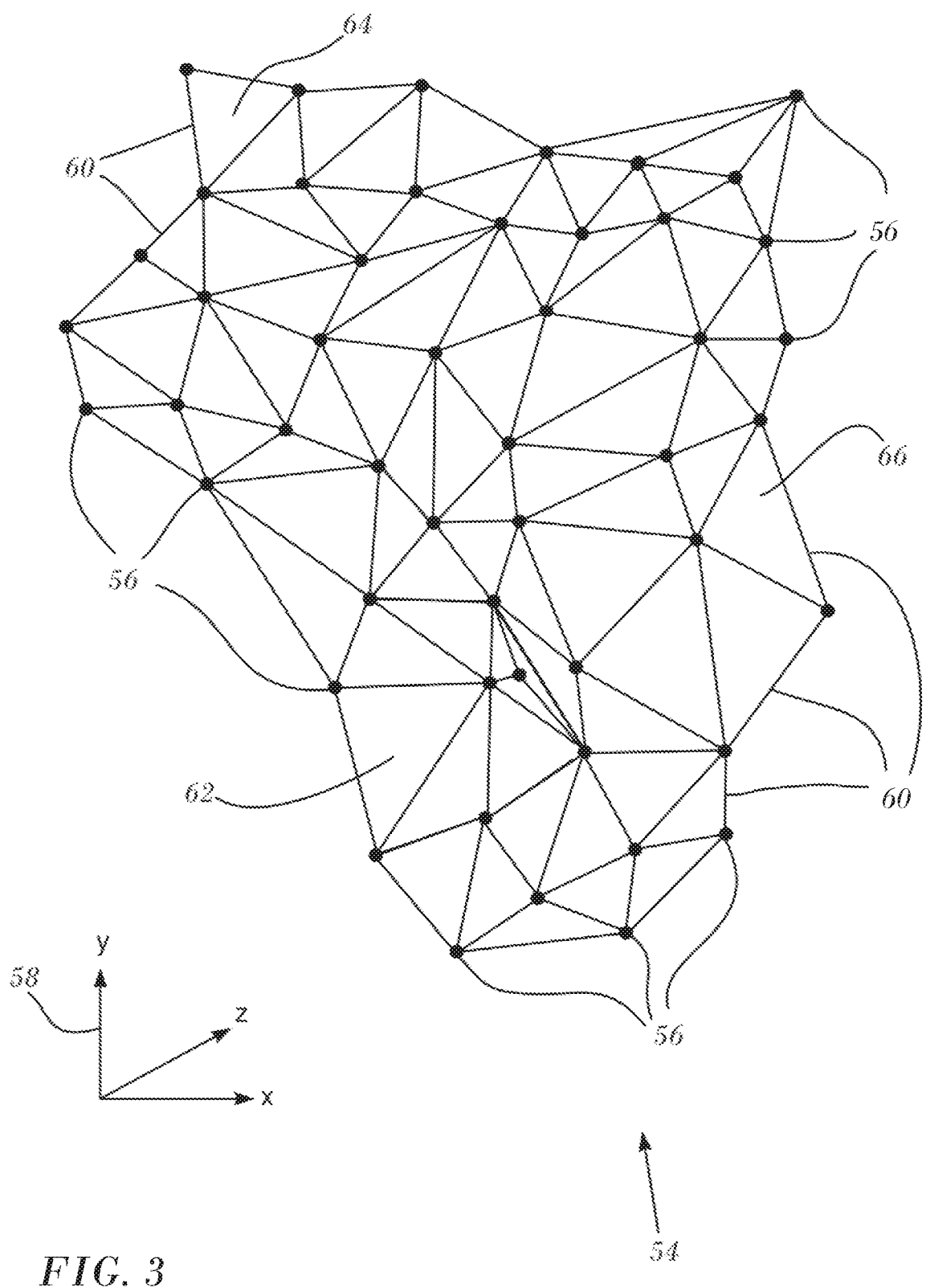
FIG. 3 is a schematic illustration of a triangular mesh in accordance with an embodiment of the invention.

At step 50 a closed 3-dimensional image representing a cardiac volume is generated using the above-described FAM technique. Then, at step 52 the epicardial surface, including the mapped locations, is modeled as a triangular mesh. Reference is now made to FIG. 3, which is a schematic illustration of a triangular mesh 54 including points 56 in accordance with an embodiment of the invention. Although a geometric mesh is shown in FIG. 3 for clarity, the triangles may be advantageously implemented as a list or an array. The points 56 are registered in step 52, when in contact with the epicardial surface of the heart 24 (FIG. 1). Typically during the mapping referred to above, image processor 21 initially stores 3-dimensional coordinates of points 56 as measured in a 3-dimensional frame of reference 58 defined by field generating coils (not shown). The image processor 21 then connects 3-dimensional coordinates of points 56, herein also termed 3-dimensional vertices, by line segments 60 to produce a set of connected 3-dimensional triangles, e.g., triangles 62, 64, 66. The procedures described in commonly assigned U.S. Patent Application Publication Nos. 20150164356, entitled Dynamic Feature Rich Anatomical Reconstruction from a Point Cloud, and 20170221254, entitled High Definition Coloring of Heart Chambers, which are herein incorporated by reference, may be used to produce the mesh 54. Other suitable algorithms include the ball-pivoting algorithm to produce the mesh 54. Alternatively, the mesh may be generated as a Delaunay triangulation. Elements of the mesh each have 3-dimensional coordinates.

Figure 4:
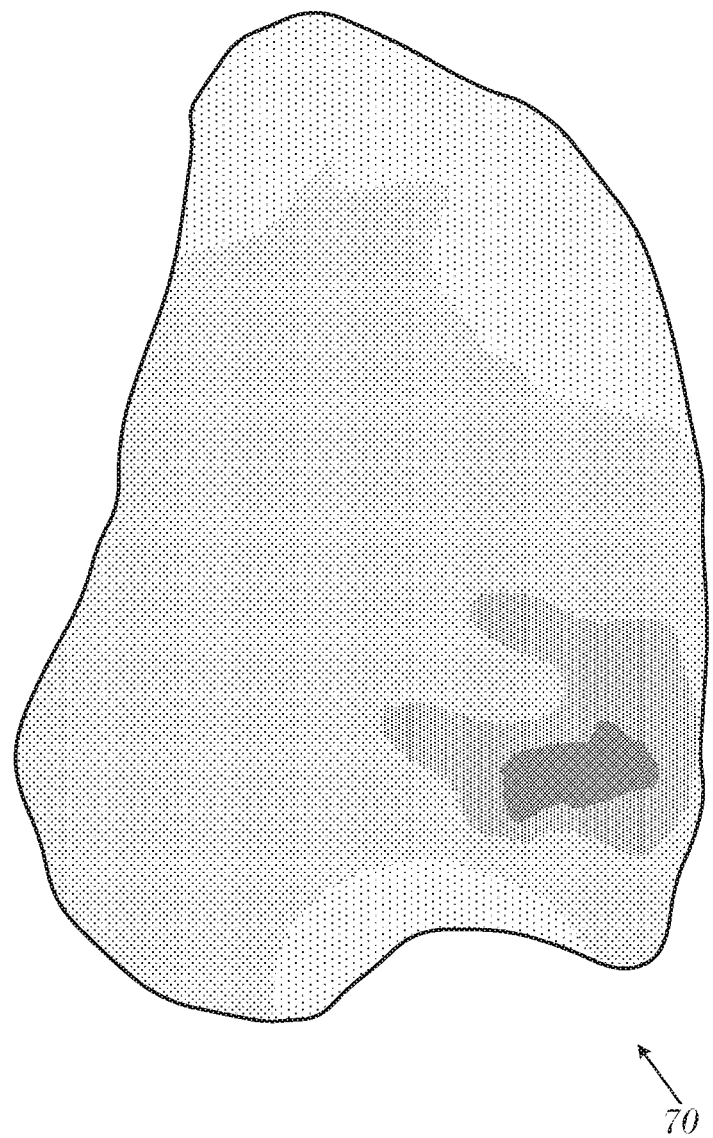
FIG. 4 is an electroanatomic map of an epicardial surface of the heart in accordance with an embodiment of the invention.

Reverting to FIG. 2, at step 68 an electroanatomical map 70 is constructed on the mesh, using the readings taken at step 48. When such a map is displayed, as shown in FIG. 4, only one side, i.e., the anterior epicardial surface, is visible-posterior aspects are invisible in this view.

Continuing to refer to FIG. 2, in step 72 the triangles of the mesh are analyzed and classified. From the perspective of an observer some of the triangles are front-facing, i.e., they face generally toward the observer, while others face away from the observer. The latter are referred to as rear-facing triangles. The terms "rear-facing" and "front-facing" are used arbitrarily herein to distinguish different orientations of the triangles in the mesh, These terms have no physical meanings with respect to the actual configuration of the mesh.

Next, in step 74 for each measured point that maps to a rear-facing triangle, the closest front-facing triangle to that point is identified.

Figure 5:
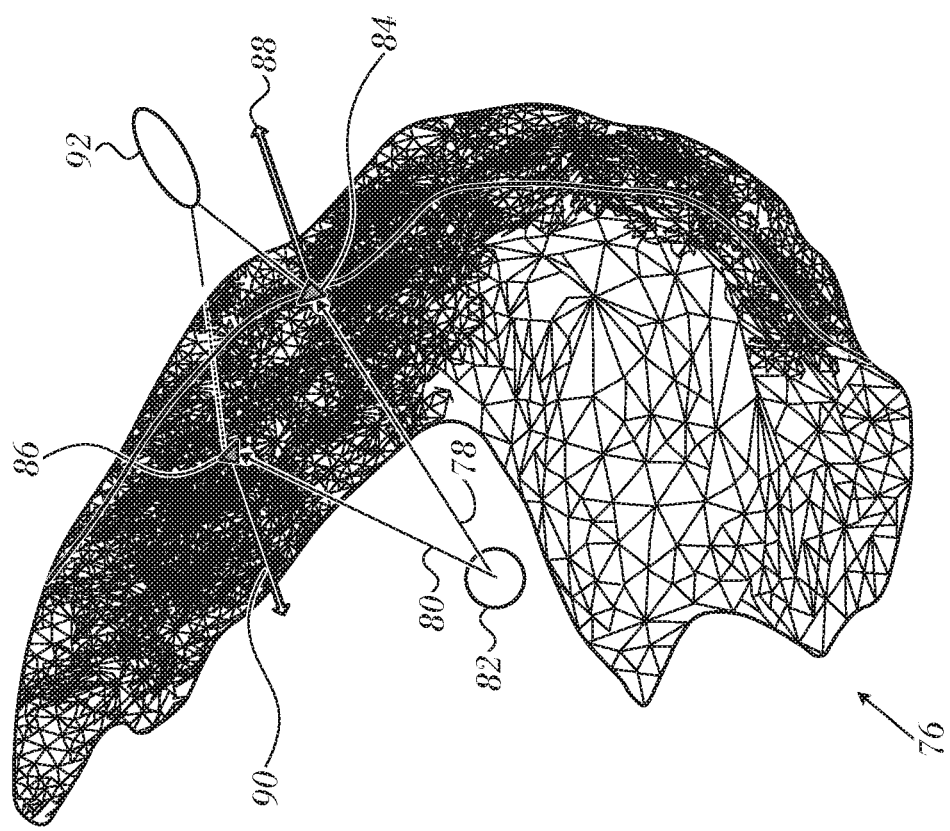
FIG. 5 illustrates a process of analyzing a triangular mesh in accordance with an embodiment of the invention.

FIG. 5 illustrates aspects of the process of step 74. A triangular mesh 76 models a cardiac volume representing the epicardium that was created by the FAM algorithm. The mesh 76 is surrounded by an exterior that includes center of mass 82 and further includes an observer 92 on the opposite side of the mesh 76. Vectors 78, 80 are directed from center of mass 82 to triangles 84, 86 on the mesh 76. Normal vectors 88, 90 are drawn from the triangles 84, 86 toward the exterior of the volume, e.g., working in a clock-wise direction. The observer 92 looking at a display screen containing the mesh 76 could see front-facing triangle 84 but could not see rear-facing triangle 86 as it is obscured by the front-facing surface of the mesh 76.

Figure 6:
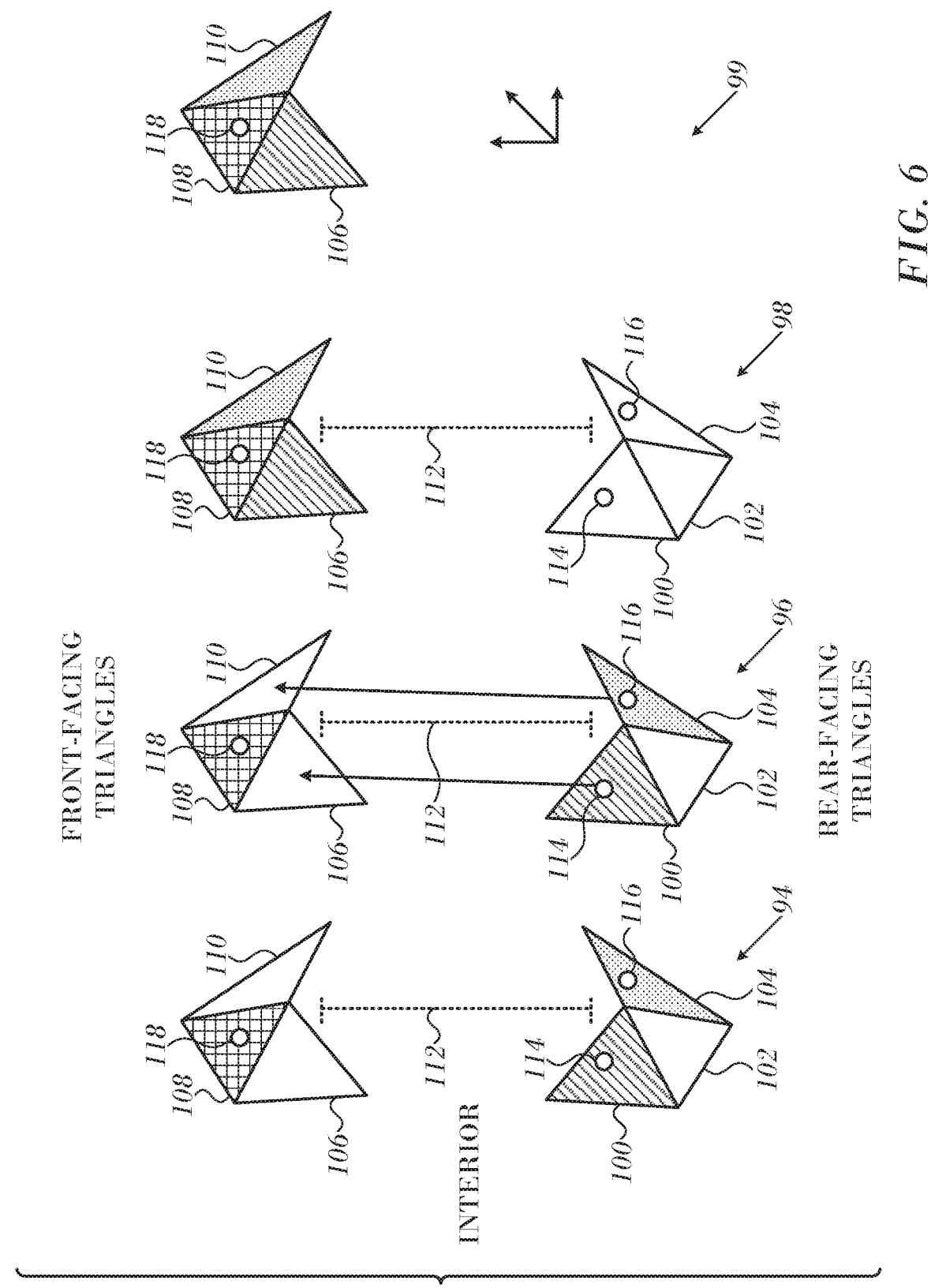
FIG. 6 is a set of diagrams of a portion of a triangular mesh that models an FAM-produced volume in accordance with an embodiment of the invention.

Projection of points that map to rear-facing triangles onto front-facing triangles is illustrated by FIG. 6, which is a set of diagrams of a portion of a triangular mesh that models an FAM-produced volume. Four phases are shown in diagrams 94, 96, 98, 99. In diagram 94 rear-facing triangles 100, 102, 104 and front-facing triangles 106, 108, 110 were identified in step 72 (FIG. 2). The two classes of triangles are separated by interior 112 of the FAM-produced volume. Measured points 114, 116 map to rear-facing triangles 100, 104, respectively. Measured point 118 maps to front-facing triangle 108. In diagram 94 the pseudocolor associated with point 118 is visible on a display, e.g., display 40 (FIG. 1). The pseudocolors associated with points 114, 116 are not visible on the display.

In diagram 96 front-facing triangles 106, 110 were identified in step 74 (FIG. 2) as the closest front-facing triangles to points 114, 116, respectively. Rear-facing triangles are omitted in the searches to find the closest triangles to the measured points.

In diagram 98 the points 114, 116 and their data are now associated with front-facing triangles 106, 110 respectively.

The front-facing triangles 106, 110 are now shown in the pseudocolors that were previously presented on rear-facing triangles 100, 104.

Figure 7:
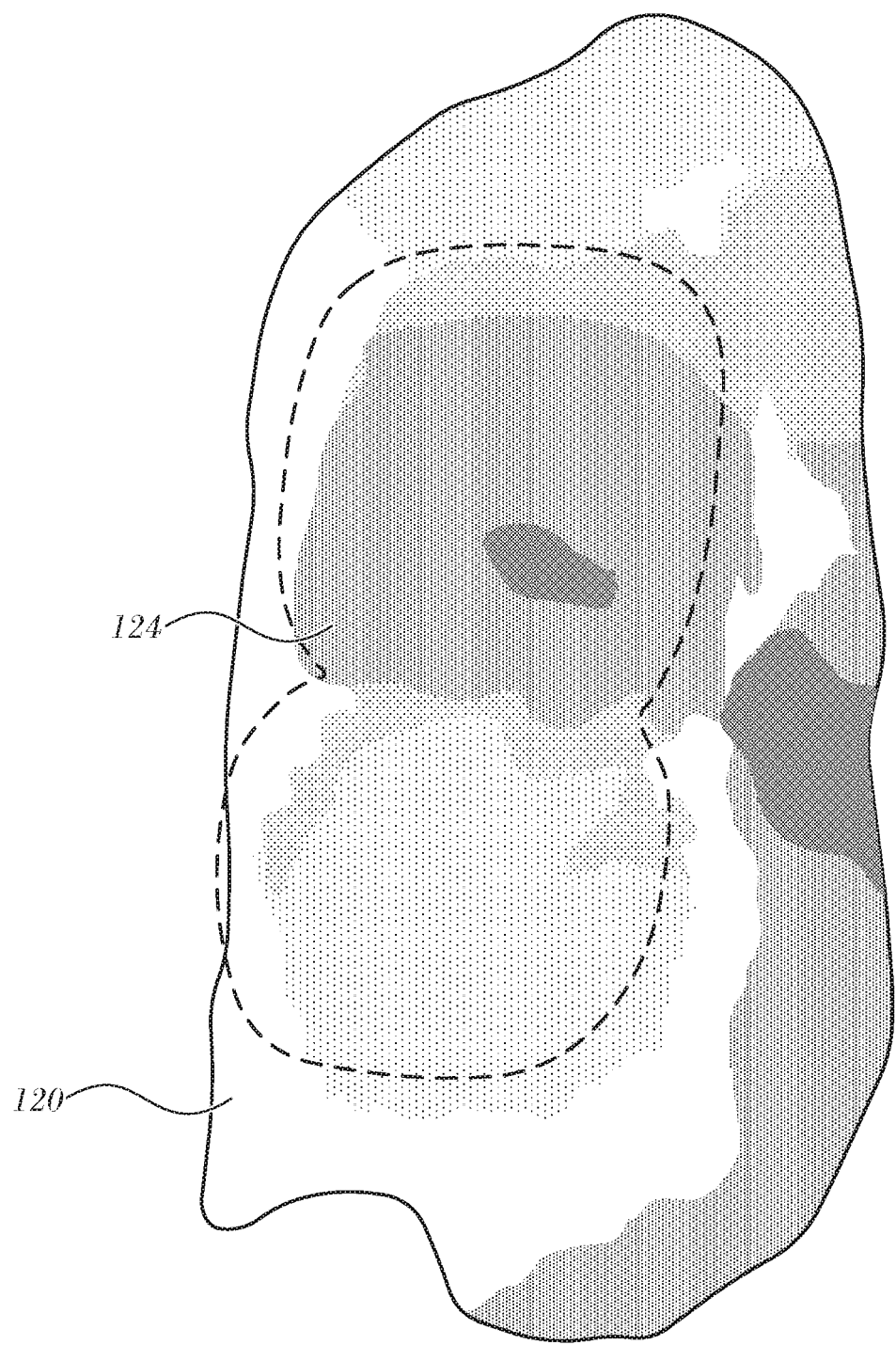
FIG. 7 illustrates projection of hidden portions of the electroanatomic map shown in FIG. 4 in accordance with an embodiment of the invention.
Figure 8:
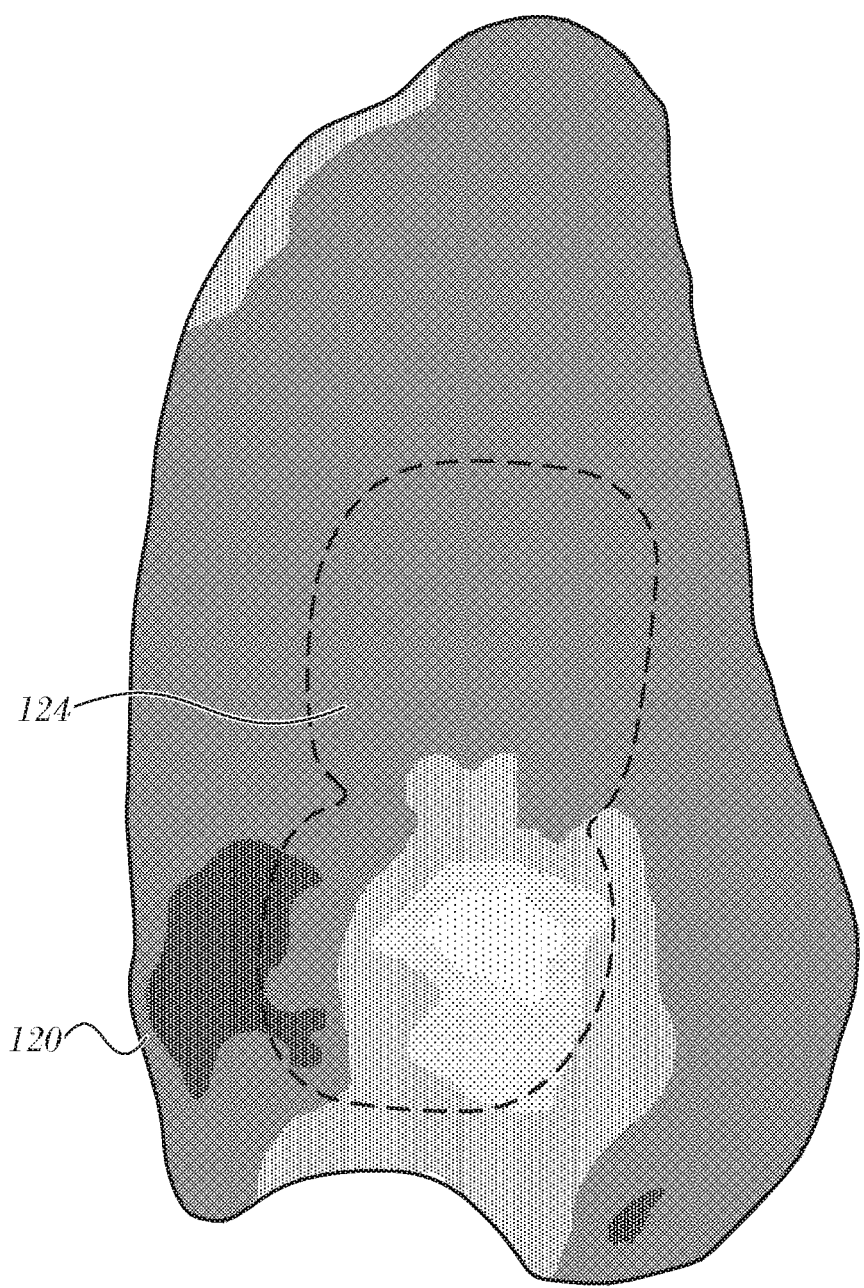
FIG. 8 is an anterior view of a corrected version of the electroanatomic map shown in FIG. 4 in accordance with an embodiment of the invention.

In diagram 99 the rear-facing triangles 100, 102, 104 have been removed. The front-facing triangles 106, 108, 110 now model the epicardial surface as a curved plane and displays a complete electroanatomic map of a portion of the epicardium. This is indicated in FIG. 2 as step 122, which can be understood with reference to FIG. 7, FIG. 8 and FIG. 9. In step 122 portions of the map taken from readings on the rear-facing surface of the volume are projected onto the front surface. These appear in FIG. 7 as area 124 (outlined by a broken line). In FIG. 8 the coloring associated the front-facing triangles is combined with the coloring of the projected points of the rear-facing triangles to form a corrected map in FIG. 8, in which the areas corresponding to the rear-facing triangles are superimposed rather than obscured. The advantage of FIG. 8 is that the areas corresponding to both front- and rear-facing triangles can be appreciated in a single view. The measured points need not encompass all rear-facing triangles, as indicated by area 120, which is outside area 124.

Figure 9:
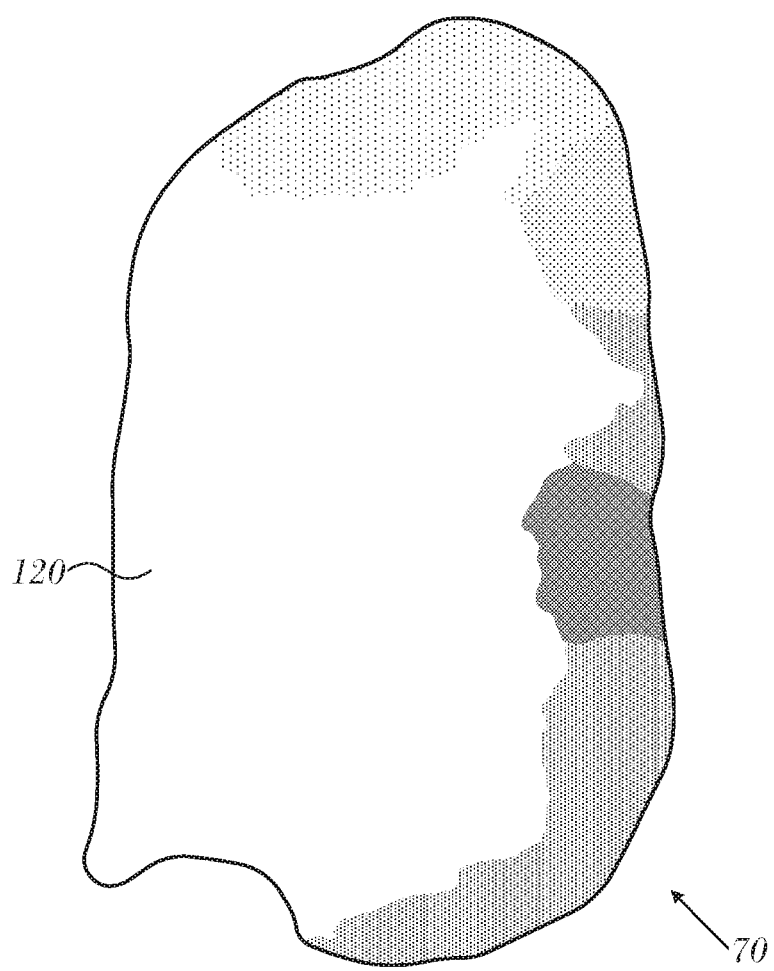
FIG. 9 is a posterior view of the surface shown in FIG. 4 in accordance with an embodiment of the invention.

In some embodiments final step 126 is performed. FIG. 9 is a posterior view of the map 70, which includes the area 120 that corresponds to rear-facing triangles of the mesh. The rear-facing triangles are removed from the mesh as shown in diagram 99 (FIG. 6). The front-facing triangles that remain in the mesh now model a curved plane with no significant thickness, and which now presents a display of the electroanatomic map that includes previously hidden data.

The above-described method can also be used to project a map taken from endocardial readings onto the front surface.

The algorithm described above is summarized by the pseudocode of Listing 1.

Listing 1

Identify the center of mass for the mesh.
For each triangle in the mesh {
    Construct a vector $\vec{A}$ from the center of mass to the triangle.
    Construct a directed vector $\vec{B}$ directed away from the center of mass and normal to the surface of the triangle.
    If the dot product $(\vec{A} \cdot \vec{B}) > 0$ {
    triangle is front-facing. It is considered in searches for a closest triangle to a hidden measured point
    }
    If the dot product $(\vec{A} \cdot \vec{B}) < 0$ {
    /* the triangle is rear-facing */
    omit this triangle from from consideration in the projection and map reconstruction that follows.
    }
}
For measured points that map to the rear-facing triangles {
    Find the closest triangle /*it will be front-facing, since rear-facing triangles have been excluded from the searches */.
    project the measured point onto the closest front-facing triangle to create a new coloring on the closest front-facing triangle based on the data associated with the measured point.
}
Recolor the map according to the projected points

Second Embodiment

Typically an FAM-produced volume is generated and during the patient session in which epicardial readings are taken. In this embodiment the FAM-produced volume is generated from images pre-acquired at a different time from the epicardial readings. The locations of the epicardial readings are then placed in registration with the FAM-produced volume by known methods, for example the methods described in commonly assigned U.S. Patent Application Publication Nos. 20130123773 entitled Integrative Atrial Fibrillation Ablation, 20160354049 entitled Registration of Coronary Sinus Catheter Image and 20160120426 entitled Registration Maps Using Intra-Cardiac Signals, all of which are herein incorporated by reference. The process described in the discussion of FIG. 2 beginning with step 52 can then be performed using the FAM-produced volume.

Implementation Details.

Figure 10:
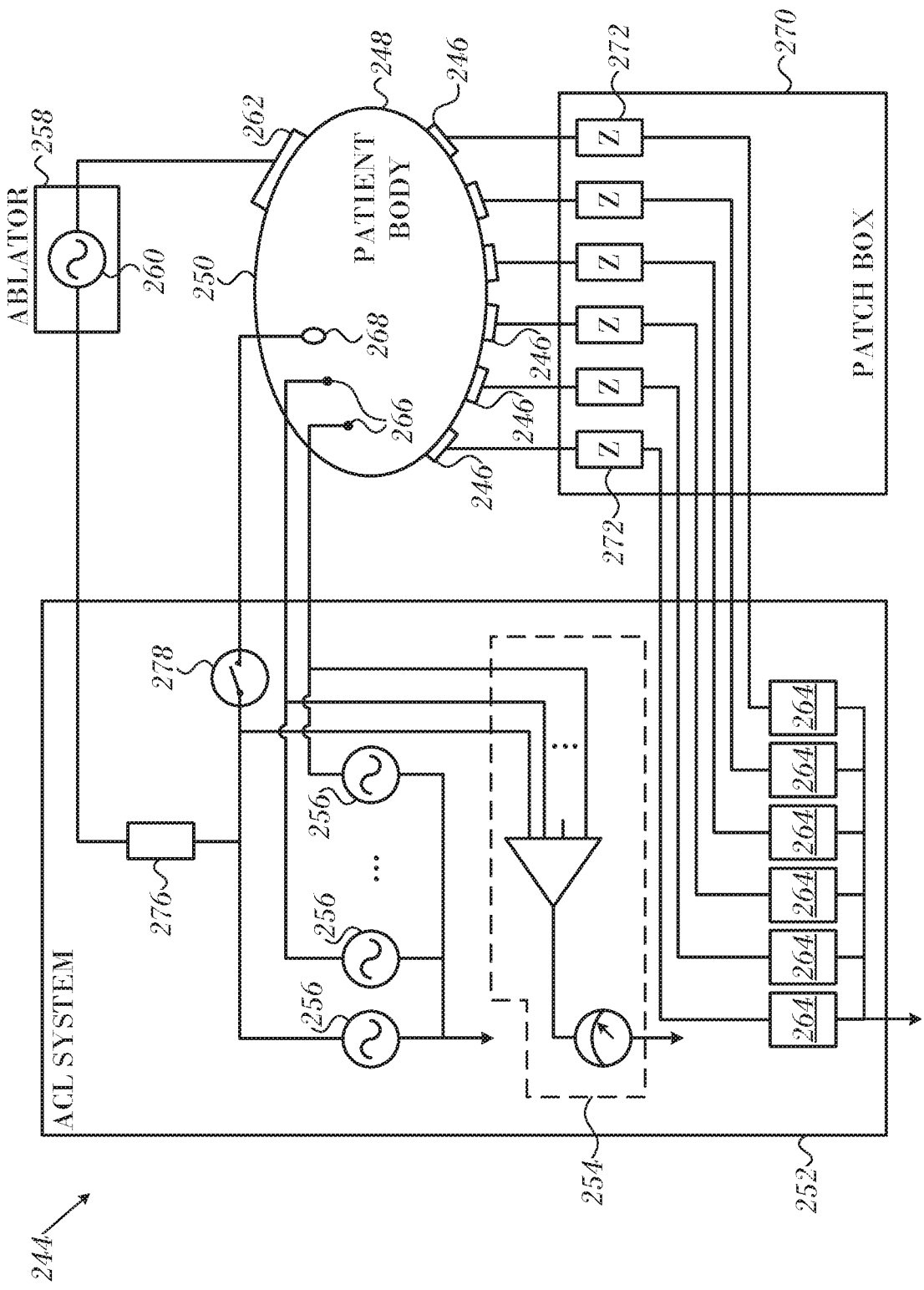
FIG. 10 is a schematic diagram of an ablation and active current location (ACL) circuit in accordance with an embodiment of the invention.

Reference is now made to FIG. 10, which is a schematic diagram of an ablation and active current location (ACL) circuit 244 for use with the system shown in FIG. 1. This arrangement is similar to that described in U.S. Patent Application Publications 2006/0173251, to Govari et al., and 2007/0038078, to Osadchy, which are herein incorporated by reference. The arrangement can be modified to operate in accordance with the principles of the present invention. A brief description follows for convenience of presentation. The (ACL) circuit 244 can be used to determine the mapped locations in step 48 (FIG. 2).

A plurality of body surface electrodes 246, which can be adhesive skin patches, are coupled to a body surface 248 (e.g., the skin) of subject 250. The body surface electrodes 246 are sometimes referred to herein as "patches". In cardiac applications the body surface electrodes 246 are usually distributed so as to surround the heart, three on the chest of the subject and three on the back. However, the number of the body surface electrodes 246 is not critical, and they may be placed at convenient locations on the body surface 248 in the general vicinity of the site of the medical procedure.

A control unit 252 includes current measurement circuitry 254 and one or more catheter electrode transmitters 256 for driving a current through one or more of the electrodes 246 to one or more of the body surface electrodes 246 at respective working frequencies. The control unit 252 is linked to a positioning processor (FIG. 1). The control unit 252 is linked to an ablator 258, which comprises at least one ablation generator 260. Currents through the body surface electrodes 246 and an ablator body surface electrode 262 flow in a circuit with the ablation generator 260 and are measured by respective current measurement circuits that are disposed within body electrode receivers 264, sometimes referred to herein as "patch measurement circuits". The body electrode receivers 264 are typically incorporated in the control unit 252. Alternatively, they may be affixed to the body surface electrodes 246. Catheter electrodes are represented as measurement electrodes 266 (circles) and a dual-purpose electrode 268 (ellipse). The dual-purpose electrode 268 functions as an ablation electrode and also serves as one of the measurement electrodes.

The body surface electrodes 246 are connected to the body electrode receivers 264 via a patch box 270, which protects the system from ablation and defibrillation currents. Typically the system is configured with six body electrode receivers 264. The patch box parasitic impedances 272 (Z), are measured during production and thus known a priori. These impedances are discussed below.

Typically, although only two measurement electrodes 266 are shown for convenience, about 80 measurement electrodes are used for impedance measurements. Typically there are one or two ablation electrodes. The coordinates of a catheter inside the body are determined in the positioning system by passing currents between electrodes on the catheter and the body surface electrodes 246.

The control unit 252 may also control an ablation circuit, comprising ablator 258, and the dual-purpose electrode 268. The ablator 258 is typically disposed externally to the control unit 252 and incorporates the ablation generator 260. It connects with the ablator body surface electrode 262 and to an ablator filter 276, which in this example is shown within the control unit 252. However this location is not essential. A switch 278 configures the ablator circuit for different modes of operation as described below. Voltage measurement circuitry is provided for determining the output of the catheter electrode transmitters 256. It will be noted from inspection that the ablation circuit is connected to one of the catheter electrode transmitters 256.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
   acquiring first electroanatomic data at first locations and second electroanatomic data at second locations on an epicardial surface of a heart;
   acquiring a closed 3-dimensional image of the epicardial surface;
   modeling the image as a 3-dimensional mesh of triangles, including rear-facing triangles and front-facing triangles;
   placing the first locations and the second locations in registration with the mesh wherein the first locations align with first front-facing triangles and the second locations align with rear-facing triangles;
   projecting the second locations onto second front-facing triangles; and
   displaying the first electroanatomic data on the first front-facing triangles and the second electroanatomic data on the second front-facing triangles,
   wherein projecting the second locations comprises:
   identifying respective closest front-facing triangles to the rear-facing triangles; and
   associating the second locations with the closest front-facing triangles.

2. The method according to claim 1, wherein displaying comprises constructing an electroanatomic map of the first locations and the second locations.

3. The method according to claim 1, wherein the mesh has a center of mass and an exterior, further comprising the steps of:
   constructing first vectors from the center of mass to each of the triangles;
   constructing second vectors from each of the triangles toward the exterior of the mesh;
   calculating respective dot products of the first vectors and the second vectors; and
   identifying the triangles as front-facing triangles and rear-facing triangles when the dot products are positive and negative, respectively.

4. The method according to claim 1, further comprising deleting the rear facing triangles from the mesh after projecting the second locations.

5. The method according to claim 1, wherein acquiring a closed 3-dimensional image is performed using a fast anatomical mapping algorithm.

6. An apparatus, comprising:
   a probe, adapted for insertion into a pericardial space of a heart, the probe comprising an elongated body, a location sensor, an ultrasound imaging transducer and at least one mapping electrode disposed on a distal portion of the body;
   a memory having programs stored therein;
   a display; and
   a processor linked to the display and being coupled to access the memory to execute the programs, the processor being connectable to receive inputs provided by the at least one mapping electrode and the ultrasound imaging transducer, wherein the programs cause the processor to perform the steps of:
   acquiring from the probe first electroanatomic data at first locations and second electroanatomic data at second locations on an epicardial surface of the heart;
   acquiring a closed 3-dimensional image of the epicardial surface;
   modeling the image as a 3-dimensional mesh of triangles, including rear facing triangles and front-facing triangles;
   placing the first locations and the second locations in registration with the mesh wherein the first locations align with first front-facing triangles and the second locations align with rear-facing triangles;
   projecting the second locations onto second front-facing triangles; and
   with the display displaying the first electroanatomic data on the first front-facing triangles and the second electroanatomic data on the second front-facing triangles,
   wherein projecting the second locations comprises:
   identifying respective closest front-facing triangles to the rear-facing triangles; and
   associating the second locations with the closest front-facing triangles.

7. The apparatus according to claim 6, wherein displaying comprises constructing an electroanatomic map of the first locations and the second locations.

8. The apparatus according to claim 6, wherein the mesh has a center of mass and an exterior, wherein the processor is further programmed to perform the steps of:
   constructing first vectors from the center of mass to each of the triangles;
   constructing second vectors from each of the triangles toward the exterior of the mesh;
   calculating respective dot products of the first vectors and the second vectors; and
   identifying the triangles as front-facing triangles and rear-facing triangles when the dot products are positive and negative, respectively.

9. The apparatus according to claim 6, wherein the processor is further programmed to delete the rear-facing triangles from the mesh after projecting the second locations.

10. The apparatus according to claim 6, wherein acquiring a closed 3-dimensional image is performed using a fast anatomical mapping algorithm.

* * * * *